United States Patent
D'Onofrio et al.

(10) Patent No.: US 11,951,269 B2
(45) Date of Patent: Apr. 9, 2024

(54) DRUG-COATED MEDICAL DEVICES

(71) Applicant: Medtronic Vascular, Inc., Santa Rosa, CA (US)

(72) Inventors: Simone D'Onofrio, Brescia (IT); Massimo Morero, Turin (IT); Bradley Steele, Plymouth, MN (US); Federica Bellucci, Alessandria (IT); Cassandra Morris, Plymouth, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1082 days.

(21) Appl. No.: 16/696,846

(22) Filed: Nov. 26, 2019

(65) Prior Publication Data

US 2020/0171281 A1 Jun. 4, 2020

Related U.S. Application Data

(60) Provisional application No. 62/772,997, filed on Nov. 29, 2018.

(51) Int. Cl.
| | | |
|---|---|---|
| *A61M 25/10* | (2013.01) | |
| *A61K 9/16* | (2006.01) | |
| *A61K 31/337* | (2006.01) | |
| *A61K 31/573* | (2006.01) | |
| *A61M 25/00* | (2006.01) | |

(52) U.S. Cl.
CPC ......... *A61M 25/104* (2013.01); *A61K 9/1676* (2013.01); *A61K 31/337* (2013.01); *A61K 31/573* (2013.01); *A61M 2025/0057* (2013.01); *A61M 2025/1031* (2013.01); *A61M 2025/105* (2013.01); *A61M 2025/1075* (2013.01); *A61M 2205/0238* (2013.01)

(58) Field of Classification Search
None
See application file for complete search history.

(56) References Cited

U.S. PATENT DOCUMENTS

| | | | |
|---|---|---|---|
| 2002/0193475 A1* | 12/2002 | Hossainy | A61L 31/146 523/105 |
| 2009/0177280 A1* | 7/2009 | Schomig | A61L 27/54 433/201.1 |
| 2011/0130829 A1 | 6/2011 | Clarke et al. | |
| 2016/0058915 A1 | 3/2016 | D'Onofrio et al. | |
| 2017/0281912 A1 | 10/2017 | Melder et al. | |
| 2017/0312484 A1* | 11/2017 | Shipley | A61M 25/104 |
| 2019/0111187 A1 | 4/2019 | Steele et al. | |
| 2020/0324092 A1* | 10/2020 | Melder | A61M 25/1027 |

FOREIGN PATENT DOCUMENTS

| | | | | |
|---|---|---|---|---|
| CN | 107261300 A | | 10/2017 | |
| CN | 107335127 A | | 11/2017 | |
| JP | 2006500987 A | * | 1/2006 | A61L 31/10 |

OTHER PUBLICATIONS

Extended European Search Report, EP Appln No. 19211294.4, 7pgs, dated Apr. 28, 2020.

\* cited by examiner

*Primary Examiner* — Susan T Tran

(74) *Attorney, Agent, or Firm* — Mueting Raasch Group

(57) ABSTRACT

A method for coating a medical device includes applying a second layer that includes a second drug on a first layer of on the medical device. The first layer includes a first drug, which may be in crystalline form. By selecting an appropriate solvent use in applying the second layer and appropriate process conditions, the second layer may be applied such that the first drug retains one or more therapeutic properties. For example, the second layer may be applied such that the first drug maintains its crystalline form. The first and second layers may be free of polymer.

17 Claims, 2 Drawing Sheets

DRUG-COATED MEDICAL DEVICES

RELATED APPLICATION

This application claims the benefit of U.S. Provisional Application No. 62/772,997, filed on 29 Nov. 2018, which provisional application is hereby incorporated herein by reference in its entirety.

FIELD

The present disclosure relates to medical devices coated with a first layer comprising a first drug and a second layer comprising a second drug, and to methods for manufacturing such coated medical devices.

BACKGROUND

Medical devices coated with multiple drugs have been described or used for many years. The drugs may be mixed and coated in a single layer or may be coated on the device in separate layers. The layers may consist essentially of the drugs or may include other excipients or polymers. In some instances, a polymer is employed to control the release rate. In some instances, the bare drug is coated on the device to facilitate rapid release and bioavailability.

Rapid release may be desirable in situations where time of contact between the device and the tissue to which the drug is delivered is minimal. For example, catheter balloons used for angioplasty procedures are often contacted with vascular tissue for short durations, and, thus, antiproliferative agents coated on the balloons for treating or preventing restenosis should be rapidly released from the balloon and transferred to the vascular tissue.

However, the effect of the transferred antiproliferative drugs should last for weeks or months because such a time frame may be important for preventing restenosis. Accordingly, a sufficiently high amount of drug should be transferred to maintain the effect during such time periods. Preferably, the antiproliferative drug is in a form that may remain active at the treated tissue for extended periods of time.

Different crystalline or amorphous forms of drugs may differ in sustained availability. For example, the morphological form of the antiproliferative drug, paclitaxel, which has been coated on medical devices, such as catheter balloons and stents, to treat and prevent restenosis, may have a substantial impact on the sustained effect of the drug. Amorphous forms of paclitaxel tend to be more rapidly released and more immediately bioavailability, relative to crystalline forms, but tend to have a less sustained therapeutic effect.

In some circumstances, it may be desirable to employ more than one drug on a medical device. For example, it may be desirable to employ an anti-inflammatory drug with an antiproliferative drug, such as crystalline paclitaxel, on balloon catheters to more effectively treat or prevent restenosis, or other comorbidities present with a stenotic lesion. Anti-inflammatory drugs, such as dexamethasone, may aid in preventing restenosis by reducing vessel wall inflammation associated with the endovascular treatment. Associated inflammation may last a few days to weeks following the procedure, and, as such, the amount of anti-inflammatory drug transferred to the tissue and the sustained effect of the anti-inflammatory drug may be less than the anti-proliferative agent.

Coating medical devices with more than one drug may affect the properties of the coating or the drugs, which may impact the therapeutic effects of the drugs. For example, including a second drug in a layer comprising the first drug may affect the release profile of the first drug, may affect the crystal morphology of the first drug, or the like. By way of a more particular example, the inclusion of a second drug in a layer comprising a first drug may result in selection of a solvent that is not ideal for the first drug, which may impact the crystal morphology of the first drug.

Coating a medical device with a first layer comprising the first drug and a second layer comprising the second drug may result in delayed release of the first drug, may adversely impact the crystalline structure of the first drug, or the like. For example, adding a polymer-free layer of dexamethasone onto a polymer-free layer comprising crystalline paclitaxel might be expected to cause the crystalline paclitaxel to at least partially dissolve in a solvent for the dexamethasone because both paclitaxel and dexamethasone are poorly water soluble, which would be expected to alter the crystalline form and/or morphology of the paclitaxel.

In sum, methods and devices coated with multiple drugs in multiple layers such that the therapeutic effect of each drug in each layer is tailored to have an intended therapeutic effect can be challenging.

SUMMARY

The present disclosure describes, among other things, medical devices coated with a first layer comprising a first drug and a second layer comprising a second drug, as well as methods for manufacturing such coated medical devices. The methods enable coating of more than one drug in more than one layer without substantially affecting an intended property of at least one of the drugs.

In some embodiments, the present disclosure describes medical devices coated with a first layer comprising an antiproliferative drug and a second layer comprising an anti-inflammatory drug, as well as methods for manufacturing such coated medical devices. For example, the antiproliferative drug may be a taxol or limus-derivative. The anti-inflammatory drug may be a nonsteroidal anti-inflammatory agent or a steroidal anti-inflammatory agent. In some embodiments, the antiproliferative agent is sirolimus or zotarolimus, and the anti-inflammatory agent is dexamethasone. One or both of the first and second layers may be free of polymers.

In some embodiments, the present disclosure describes medical devices coated with a first layer comprising a crystalline first drug and a second layer comprising a second drug, as well as methods for manufacturing such coated medical devices. The methods enable coating of the second layer with the second drug on the first layer without substantially affecting the crystal form of the first drug. For example, the methods disclosed are suitable for maintaining crystalline paclitaxel when applying a subsequent layer comprising dexamethasone.

In various embodiments described herein, a method for coating a medical device comprises applying a second layer comprising a second drug on a first layer of on the medical device. The second layer is applied such that the first drug maintains an intended property. One or both of the first and second layers may be free of polymer. In some embodiments, both the first and second layers are free of polymer. In some embodiments, the first drug is an antiproliferative drug and the second drug is anti-inflammatory drug. For example, the antiproliferative drug may be a taxol or limus-derivative. The anti-inflammatory drug may be a nonsteroidal anti-inflammatory agent or a steroidal anti-inflammatory agent. In some embodiments, the antiproliferative agent is sirolimus or zotarolimus, and the anti-inflammatory agent is dexamethasone.

In some embodiments, a method for coating a medical device comprises applying a second layer comprising a second drug on a first layer of on the medical device. The first layer comprises a first drug in crystalline form. The second layer is applied such that the first drug maintains its crystalline form. One or both of the first and second layers may be free of polymer. In some embodiments, both the first and second layers are free of polymer.

The method may include providing a solution comprising the second drug and a solvent and spraying the solution on the first layer of the medical device under conditions that enable deposition of the second layer on the first layer such that the first drug maintains its crystalline form. The second drug is preferably highly soluble in the solvent so that a sufficient amount of the second drug may be applied in the second layer with a relatively small volume of solution to minimize interaction and potential dissolution of the first drug in the first layer. The solvent is preferably chosen such that the solubility of the second drug in the solvent is greater than the solubility of the first drug in the solvent. It will be understood that the desire of minimizing volume, and thus maximizing solubility of the second drug in the solvent, should be balanced against the desirability to have the second drug have a relatively higher solubility in the solvent. Accordingly, in instances where the first drug is highly soluble in a first solvent, a suitable alternative solvent having lower solubility for the first drug may be chosen even if the first solvent provides for lower volumes for dissolving the second drug. The solvent is preferably chosen to be relatively volatile to enable evaporation of much of the solvent prior to contacting the first layer. The desirability for a relatively high volatility should be balanced against the desire for minimal volume (and maximum solubility of the second drug) and the desire to have a relatively higher solubility of the second drug relative to the first drug. Accordingly, factors to consider in choosing an appropriate solvent for depositing the second drug on the first layer include (i) solubility of the second drug in the solvent and, thus, volume of solution needed to apply suitable amount of the second drug; (ii) relative solubility of the first and second drugs in the solvent; and (iii) volatility of the solvent.

Process conditions may also be selected to reduce the impact of the solvent on the first drug in the first layer when a solution comprising the solvent and the second drug are sprayed on the first layer. For example, the fineness of the spray and the distance from the surface of the first layer may be varied to reduce the impact of the solvent on the first drug. A finer spray and a larger distance, for example, may result in more evaporation of the solvent prior to contacting the first layer. In addition, the temperature of a spray nozzle or the ambient temperature may affect the amount of solvent that reaches the first layer, which higher temperatures tending to lead to greater evaporation of the solvent prior to reaching the first layer. The stability of the drugs at the elevated temperatures should be considered.

In various embodiments described herein, a medical device includes a first coating layer comprising a first crystalline drug and a second layer comprising a second drug. The first layer may comprise crystalline paclitaxel. The first layer may comprise crystalline paclitaxel and urea. The second layer may comprise dexamethasone. The second layer may comprise dexamethasone and urea. In some embodiments, the first layer comprises crystalline paclitaxel or crystalline paclitaxel and urea, and the second layer comprises dexamethasone or dexamethasone and urea. One or both of the first and second layers may be free of a polymer.

Advantages of one or more of the various embodiments presented herein over prior coating methods, coated medical devices, treatment modalities, or the like will be readily apparent to those of skill in the art based on the following detailed description when read in conjunction with the accompanying drawings.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

In this disclosure, terms such as "a," "an," and "the" are not intended to refer to only a singular entity but include the general class of which a specific example may be used for illustration. The terms "a," "an," and "the" are used interchangeably with the term "at least one."

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise. The term "and/or" means one or all of the listed elements or a combination of any two or more of the listed elements.

Also herein, unless otherwise specified, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used.

Also herein, the recitations of numerical ranges by endpoints include all numbers subsumed within that range as well as the endpoints (e.g., 1 to 5 includes 1, 1.5, 2, 2.75, 3, 3.80, 4, 5, etc.). Herein, "up to" a number (e.g., up to 50) includes the number (e.g., 50).

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Figure 1:
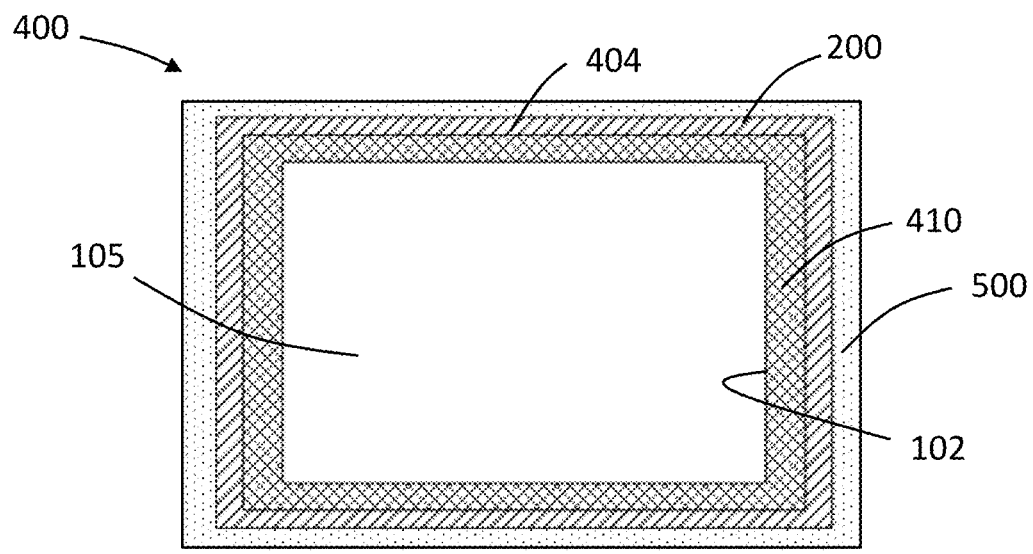
FIG. 1 is a schematic sectional view of an embodiment of a medical device having a coating comprising a nanoparticle or microparticle for releasing a therapeutic agent.

The schematic drawings presented herein are not necessarily to scale.

DETAILED DESCRIPTION

In the following detailed description, reference is made to the accompanying drawings that form a part hereof, and in which are shown by way of illustration several specific embodiments of devices, systems and methods. Like numbers used in the figures refer to like components and steps. However, it will be understood that the use of a number to refer to a component in a given figure is not intended to limit the component in another figure labeled with the same number. In addition, the use of different numbers to refer to components in different figures is not intended to indicate that the different numbered components cannot be the same as, or similar to, other numbered components. It is to be understood that other embodiments are contemplated and may be made without departing from the scope or spirit of the present disclosure. The following detailed description, therefore, is not to be taken in a limiting sense.

This disclosure relates to, among other things, coating methods and drug-coated medical devices. The devices are coated with a first layer comprising a first drug and a second layer comprising the second drug. The first layer is closer to a body of the device than the second layer. In other words, the second layer is on top of the first layer. The second layer is preferably coated on the first layer such that one or more or all the intended properties of the first layer is maintained.

When the first and second layers are coated on a device that is intended to contact a target tissue for a short period of time, the first and second layers are preferably free of polymers so that the drugs may be rapidly released from the device when the device contacts the target tissue.

Preferably, the first drug in the first layer is a drug that is required to be present at higher concentrations or for longer durations at the target tissue than the second drug in the second layer. Some of the second drug in the second layer may be lost prior to the device reaching the target tissue, while the first drug in the first layer may be protected from loss by the second layer. Such orientations may be particularly relevant where the device may be subjected to passage through bodily fluid, such as through the vasculature of a patient. When moving a device through the vasculature, the outer most drug-containing layers may be most susceptible to drug loss prior to reaching the target tissue, particularly if the layer is polymer free.

Preferably, the second layer is coated on the first layer in a manner that maintains distinct first and second layers rather than causing the first and second layer to mix to a substantial degree. Such separation of layers may allow for differential delivery of the drugs in the layers to the target tissue and may allow for differential loss of drug in the process of orienting the device at the target tissue, such as tracking the device through a patient's vasculature.

When the first drug in the first layer is preferably in a crystalline form, the second layer comprising the second drug is preferably coated on the first layer in a manner that maintains the crystalline form of the first drug. The drug in the second layer may be in a crystalline form, an amorphous form, or a combination of crystalline and amorphous forms.

Any suitable medical device may be coated with the first layer and the second layer. Preferably, the medical device is a device for intravascular use. For example, the medical device may be a balloon catheter, a drainage catheter, a replacement or artificial venous valve, an aortic valve, a replacement valve, a ventricular catheter, a ventriculostomy balloon, a balloon or self-expandable stent, or a coronary balloon.

Preferably, the medical device comprises a balloon catheter. The first layer and second layers may be placed on a balloon of any suitable balloon catheter. The balloons may be compliant, semi-compliant or non-compliant. The balloons may be formed from any suitable material. For example, the balloons may be formed of polyamides, polyethylene terephthalate (PET), polyurethane, latex, silicone, polyethylene (PE), polypropylene (PP), polyetherimide (PEI), polytetrafluoroethylene (PTFE), ethylene tetrafluoroethylene (ETFE), fluorinated ethylene propylene (FEP), polyoxymethylene (POM), polybutylene terephthalate (PBT), polyether-block-ester, polyvinylchloride (PVC), polyether-block-amide, polyetheretherketone (PEEK), polyimide (PI), polyphenylene sulfide (PPS), polyphenylene oxide (PPO), poly(ethylene naphthalenedicarboxylate) (PEN), polysulfone, perfluoro(propyl vinyl ether) (PFA), or mixtures, combinations, copolymers thereof, and the like. In some embodiments, the balloon is made of nylon 12.

In some embodiments, the medical device coated with the first and second layer is a stent. The stent may be balloon-expandable or self-expanding.

The sent may comprise a frame comprising one or more of a variety of biocompatible metals such as stainless steel, titanium, magnesium, aluminum, chromium, cobalt, nickel, gold, iron, iridium, chromium/titanium alloys, chromium/nickel alloys, chromium/cobalt alloys, such as MP35N and L605, cobalt/titanium alloys, nickel/titanium alloys, such as nitinol, platinum, and platinum-tungsten alloys. The metal composition gives the stent framework the mechanical strength to support the lumen wall of the vessel and sufficient longitudinal flexibility so that it can be transported through the cardiovascular system. For example, the stent may be made of nitinol. In some embodiments, the stent is made of stainless steel.

The stent may comprise a polymeric frame that may be biodegradable, biostable, or comprise a mixture of polymeric materials that are both biostable and biodegradable. Biodegradable polymers appropriate for the stents include polylactic acid, polyglycolic acid, and their copolymers, caproic acid, polyethylene glycol, polyanhydrides, polyacetates, polycaprolactones, poly(orthoesters), polyamides, polyurethanes and other suitable polymers. Biostable polymers appropriate for the stents include polyethylene, polypropylene, polymethyl methacrylate, polyesters, polyamides, polyurethanes, polytetrafluoroethylene (PTFE), polyvinyl alcohol, and other suitable polymers. These polymers may be used alone or in various combinations to give the stent unique properties such as controlled rates of degradation.

The stent frame may be formed by shaping a metallic wire or polymeric filament, or by laser cutting the stent from a metallic or polymeric sheet, or any other appropriate method. The surface of the stent framework may be cleaned by washing with surfactants to remove oils, mechanical polishing, electropolishing, etching with acid or base, or any other effective means to expose a clean, uniform surface that is ready for applying a coating The first and second layer applied to the medical device, such as a balloon or a stent, may comprise any suitable drug. The drugs employed may depend on the nature of the device and its use. For example, if the device is balloon catheter, the drugs may be employed to treat or prevent vascular disease or associated symptoms.

Non-limiting examples of drugs that may be employed include, but are not limited to, anti-restenosis agents, anti-proliferative agents, antibiotic or antimicrobial agents, antimitotic agents, antiplatelet agents, vasodilators, alkylating agents, platinum coordination complexes, hormones, anti-coagulants, fibrinolytic agents, thrombolytic agents, antimigratory agents, antisecretory agents, anti-inflammatory agents, antioxidants, indole acetic acids, indene acetic acids, immunosuppressive agents, angiogenic agents, angiotensin receptor blockers, nitric oxide donors, anti-sense oligonucleotides, cell cycle inhibitors, mTOR inhibitors, growth factor receptor signal inhibitors, transduction kinase inhibitors, retinoids, cyclin/CDK inhibitors, HMG co-enzyme reductase inhibitors, and protease inhibitors. In some embodiments, the device comprises a balloon made of nylon-12 coated with an antiproliferative agent as a first layer.

In some embodiments, one or both of the first or second layers may comprise one or more of heparin or another thrombin inhibitor, hirudin, hirulog, argatroban, D-phenyl-alanyl-L-poly-L-arginyl chloromethyl ketone or another antithrombogenic agent, or mixtures thereof; urokinase, streptokinase, a tissue plasminogen activator, or another thrombolytic agent, or mixtures thereof; a fibrinolytic agent; a calcium channel blocker, a nitrate, nitric oxide, a nitric oxide promoter or another vasodilator; an antimicrobial agent or antibiotic; aspirin, ticlopdine or another antiplatelet agent; colchicine or another antimitotic, or another microtubule inhibitor; cytochalasin or another actin inhibitor; a remodeling inhibitor; deoxyribonucleic acid, an antisense nucleotide or another agent for molecular genetic intervention; GP IIb/IIIa, GP Ib-IX or another inhibitor or surface glycoprotein receptor; methotrexate or another antimetabolite or antiproliferative agent; an anticancer chemotherapeutic agent; dexamethasone, dexamethasone sodium phosphate, dexamethasone acetate or another dexamethasone derivative, or another anti-inflammatory steroid; dopamine, bromocriptine mesylate, pergolide mesylate or another dopamine agonist; a radiotherapeutic agent; a peptide, a protein, an enzyme, an extracellular matrix component, a cellular component or another biologic agent; captopril, enalapril or another angiotensin converting enzyme (ACE) inhibitor; alphatocopherol, superoxide dismutase, deferoxyamine, a 21-aminosteroid (lasaroid) or another free radical scavenger, iron chelator or antioxidant; and angiopeptin.

In various embodiments, one or both of the first and second layer comprises an anti-restenosis therapeutic agent. For example, the first or second layer may comprise an anti-proliferative agent, an anti-mitotic agent, or the like. One or more taxol or limus-derivative may be employed as an anti-restenosis therapeutic agent. Some non-limiting examples of anti-restenosis agents are rapamycin, taxol, paclitaxel, doxetaxel, sirolimus, rapamycin, everolimus, zotarolimus, and the like. In some embodiments, a balloon made of nylon-12 is coated with paclitaxel as a first layer.

In some embodiments, one or both of the first and second layer comprises an anti-inflammatory agent. Anti-inflammatory agents, such as steroid anti-inflammatory agents and non-steroidal anti-inflammatory agents may be used. For example, anti-inflammatory agents may include glucocorticoids or cyclooxygenase (COX) inhibitors. Non-limiting examples of suitable anti-inflammatory agents include diclofenac, hydrocortisone, prednisone, prednisolone, beclomethasone, betamethasone, dexamethasone, and the like. In some embodiments, a balloon made of nylon-12 is coated with paclitaxel as a first layer and dexamethasone as a second layer.

In some embodiments, one or both of the first and second layer comprises a therapeutic agent to disrupt a blood clot, such as a thrombolytic agent. Non-limiting examples of thrombolytic agents include tissue plasminogen activator (TPA), streptokinase, urokinase, tenecteplase, rokinase, reteplase, anistreplase, and the like.

Unless content clearly dictates otherwise, general reference to a drug in the present disclosure includes reference to salts of the drug, hydrates of the drug, polymorphs of the drug, isomers of the drug (including constitutional isomers and stereoisomers such as enantiomers and diasteriomers), and the like.

In some embodiments, a drug-containing layer (e.g., one or both of the first and second layer) includes one or more polymorphs of a drug. Polymorphs may have different solubilities or crystal forms. Polymorphs may have characteristics that affect tissue uptake of the drug at the delivery site or dissolution rate in bodily fluids. The polymorph(s) may be selected to facilitate a particular therapeutic objective.

The first and second layer may include drug particles having any suitable size profile. Preferably, the particulate size profile facilitates uptake by the tissue. Very small particles, such as particles less than 1 µm in size, may be taken up directly into arterial tissue. In some embodiments the drug-containing layer includes a drug in a particulate form that has a particle size in a range from 0.01 µm to 20.0 µm. Multi-modal ranges, prepared, e.g. by mixing two or more sets of different size ranges may be used in some cases to provide a desired bioavailability profile over time. For example, smaller crystals will more readily dissolve and enter the tissue for immediate effect, while larger crystals will dissolve at a slower rate enabling longer drug persistence.

One or both of the first layer and the second layer may include drug in crystalline or amorphous form. In some embodiments, one or both of the first and second layers includes a drug in both an amorphous and a crystalline form. In some embodiments, one or both of the first layer and the second layer may include a drug in more than one crystalline form.

One or both of the first layer and the second layer preferably comprises one or more drugs in a therapeutically effective amount. As used herein, "therapeutically effective amount" means a drug amount capable of inducing a therapeutic or preventive effect against the disease being treated or prevented. For example, if the disease being treated or prevented is restenosis of vascular tissue, the one or more drugs present in the drug-containing layer may be present in an amount effective to treat or prevent restenosis of the treated vascular tissue in the patient.

One or both of the first layer and the second layer may comprise one or more drugs in any suitable density. For example, the drug may be present in the drug-containing layer at a density from about 0.1 µg/mm$^2$ to about 100 µg/mm$^2$, such as from about 0.1 µg/mm$^2$ to about 10 µg/mm$^2$ or from about 0.1 µg/mm$^2$ to about 5 µg/mm$^2$. In some embodiments, the drug is present in the drug-containing layer at a density of about 0.25 µg/mm$^2$ to about 20 µg/mm$^2$. By way of example, the first drug-containing layer may include paclitaxel in an amount ranging from 0.5 µg/mm$^2$ to 20 µg/mm$^2$, preferably between 1 µg/mm$^2$ and 7 µg/mm$^2$, more preferably between 3 µg/mm$^2$ and 5 µg/mm$^2$, and the second drug-containing layer may comprise dexamethasone in an amount ranging from 1 µg/mm$^2$ to 20 µg/mm$^2$, preferably between 1 µg/mm$^2$ and 10 µg/mm$^2$.

In some embodiments, one or both of the first layer and the second layer comprises one or more of zotarolamus, sirolimus, dexamethasone and paclitaxel.

In some embodiments, the first layer comprises an anti-restenosis agent and the second layer comprises an anti-inflammatory agent, and the device is an endovascular device. The device may comprise a balloon or a stent. The anti-restenosis agent may be paclitaxel, and the anti-inflammatory agent may be dexamethasone. The paclitaxel may treat or prevent restenosis due to its antiproliferative effects, and the dexamethasone may aid in preventing restenosis by reducing vessel wall inflammation associated with the endovascular treatment.

Preferably, the first layer comprises paclitaxel and is used to treat restenosis. Preferably, at least some or all of the paclitaxel is in anhydrous crystalline form. Preferably, the first layer provides for immediate release and bioavailability of a therapeutically effective amount of paclitaxel when the medical device on which the paclitaxel is coated is contacted with tissue in the patient.

As used herein paclitaxel in "anhydrous crystalline form" means paclitaxel essentially free from water of crystallization. Anhydrous crystalline paclitaxel may be obtained by direct crystallization, or hot and/or vacuum drying, of a hydrated or solvated hydrated form.

In some embodiments when the first layer comprises paclitaxel all the paclitaxel is crystalline paclitaxel, or the paclitaxel is a mixture of amorphous and crystalline paclitaxel. For example, the fraction of the paclitaxel that is amorphous may be from 0% to 25%, such as about 1% to about 5%, based on total paclitaxel weight. The fraction of the paclitaxel that is crystalline may be, for example, from 1% to 100%, such as from about 75% to about 100%, based on the total paclitaxel weight. The fraction of the paclitaxel that is anhydrous may be 5% to 100%.

The first layer comprising paclitaxel may also comprise urea. The presence of urea in a paclitaxel-containing layer may promote the release of the paclitaxel. The second layer may comprise urea. The presence of urea in the second layer in proximity to, or in contact with, a first layer comprising paclitaxel may promote the release of the paclitaxel and may promote the release of the second drug.

In some embodiments, the paclitaxel is immediately released and bioavailable at the site of intervention.

As used herein, "an immediate release and bioavailability" means a release from the medical device surface in periods of time ranging between 1 second and 1.5 minutes, preferably between 20 seconds and 1 minute, and an absorption by the tissue in periods of time ranging between 1 second and 25 minutes, preferably between 20 seconds and 25 minutes.

As used herein, "site of intervention" means, when describing use in a blood vessel, the section of the blood vessel treated directly with a medical device, such as a catheter balloon, and the adjacent portion in the tissues of which the post-procedure presence of the drug can be detected. Generally, such section will extend for 2 to 10 mm down- and upstream of the contact section with the balloon.

The first and second drug may be present in any suitable coating composition and may be applied to the surface of the medical device in any suitable matter. Preferably, the coating composition comprising the first drug does not include a polymer. Preferably, the coating composition comprising the second drug does not include a polymer.

The coating composition comprising the first drug may be applied to a surface of the medical device in any suitable manner to result in a first layer having a crystalline first drug. For example, an anhydrous crystalline form of paclitaxel may be obtained by dissolving paclitaxel in an aqueous solvent, by completely or partially wetting the surface of the device with such solution, and by letting the solvent evaporate, naturally or by hot or vacuum drying, to the formation of a crystalline layer having a white, homogeneous, or partially inhomogeneous appearance. As the aqueous solvent, a mixture of solvents selected from acetone/ethanol/water, tetrahydrofuran/water, methanol/water, acetone/water, ethanol/water, acetonitrile/water, DMF/water is preferably used More preferably, the solvent is a 9:1 tetrahydrofuran/water mixture or a tetrahydrofuran/water mixture with ratios ranging between 9.5:0.5 and 65:35, or an acetone/ethanol/water mixture in which the organic solvent is present in amounts not less than 50% by volume relative to water.

A first layer comprising paclitaxel may also comprise urea. Paclitaxel may be dissolved in an appropriate solvent in the presence of urea and coated on the surface of the medical device. Urea may be used in any suitable amount, such as from 1 mg per mL to 100 mg per mL solvent, preferably from 4 mg per mL to 10 mg per mL solvent, more preferably about 7 mg per mL solvent. In some preferred embodiments, the paclitaxel and urea comprise at least 90% of the weight of the drug-containing layer, such as at least 95% or 99% of the weight of the first layer.

Other excipients that may be included in a first layer comprising paclitaxel include bioabsorbable agents, microspheres, microtubes, and physiologically compatible non-reactive drug transfer or radio opaque agents, such as iopromide, cremophore EL, vitamin E, Tocopheryl Polyethylene Glycol Succinate (TPGS), polyethylene glycol (e.g., PEG 8000), triglyceride, and the like.

A liquid composition, such as a solution, comprising the second drug may be sprayed onto a surface of the device on which the first layer is disposed in any suitable manner, provided that the first drug in the first layer maintains its crystalline form. Solvents and process conditions may be selected to achieve such a result.

The second drug may have any suitable solubility in the solvent. Preferably, the second drug is highly soluble in the solvent so that a sufficient amount of the second drug may be applied in the second layer with a relatively small volume of solution to minimize interaction and potential dissolution of the first drug in the first layer. For example, 5 milligrams or more of the second drug may be soluble in 1 ml of the solvent. In some embodiments, 10 milligrams or more of the second drug may be soluble in 1 ml of the solvent. In some embodiments, 20 milligrams or more, or 25 milligrams or more, of the second drug is soluble in 1 mL of the solvent.

The second drug may have any suitable solubility in the solvent relative to the first drug. Preferably, the second drug has a solubility in the solvent that is higher than the solubility of the first drug in the solvent. For example, the second drug is preferably 1.5 times or more soluble in the solvent than the first drug. In some embodiments, the second drug is 2 times or 3 times or more soluble in the solvent than the first drug. It will be understood that the desire of minimizing volume, and thus maximizing solubility of the second drug in the solvent, should be balanced against the desirability to have the second drug have a relatively higher solubility in the solvent. Accordingly, in instances where the first drug is highly soluble in a first solvent, a suitable alternative solvent having lower solubility for the first drug may be chosen even if the first solvent provides for lower volumes for dissolving the second drug.

The solvent may have any suitable degree of volatility. The solvent for the second drug preferably is sufficiently volatile to enable evaporation of some of the solvent prior to contacting the first layer. For example, the solvent may have a vapor pressure of 0.0005 atmosphere or greater at 20° C. In some embodiments, the solvent has a vapor pressure of 0.03 atmosphere or greater at 20° C., such as a vapor pressure of 0.07 atmosphere or greater at 20° C., or 0.1 atmosphere or greater at 20° C. The desirability for a relatively high volatility should be balanced against the desire for minimal volume (and maximum solubility of the second drug) and the desire to have a relatively higher solubility of the second drug relative to the first drug.

The solvent for the second drug may include any one or more compounds and may depend on the first and second drugs employed. In some embodiments, the second drug is dexamethasone and the solvent comprises one or more of tetrahydrofuran (THF), acetone, methanol, acetonitrile, dimethyl sulfoxide dioxane (DMSO), ethanol, acetone and water. If the solvent for dexamethasone comprises water, the solvent preferably comprises less than 20%, such as less than 15%, water by volume.

The liquid composition comprising the second drug may comprise any other suitable compounds.

For example, the solution comprising the second drug may comprise urea. The liquid composition may comprise any suitable amount of urea. Urea may be used in any suitable amount, such as from 1 mg per mL to 100 mg per mL solvent, from 4 mg per mL to 10 mg per mL solvent, or about 7 mg per mL solvent. Any suitable solvent may be used. For example, the liquid composition may comprise methanol or ethanol. In some embodiments, the liquid composition comprises about 100% methanol or about 99% ethanol. In some embodiments, the second drug and urea comprise at least 90% or the weight of the resulting second layer, such as at least 95% or 99% of the weight of the second layer.

In some embodiments, the liquid composition for forming the second layer comprises dexamethasone and urea. The liquid composition may comprise any suitable ratio (by weight) of dexamethasone and urea. For example, the liquid composition may comprise a ratio from about 10:1 (dexamethasone:urea) to about 1:10 (dexamethasone: urea), such as from about 5:1 (dexamethasone:urea) to about 1:5 (dexamethasone: urea), or about 1:1 (dexamethasone:urea). The liquid composition comprising dexamethasone and urea may comprise any suitable solvent, such as a solvent comprising methanol or ethanol. In some embodiments, the liquid composition comprising dexamethasone and urea comprises methanol as a solvent or ethanol:water, such as about 99:1 (ethanol:water), as a solvent. In some embodiments, the dexamethasone and urea comprise at least 90% or the weight of the resulting second layer, such as at least 95% or 99% of the weight of the second layer.

Any suitable process conditions may be employed for spraying a liquid composition comprising the second drug and the solvent on the device onto which the first layer has previously been applied. Preferably, the process conditions are selected to reduce the impact of the solvent on the first drug in the first layer when the solution is sprayed on the first layer. For example, the fineness of the spray and the distance from the surface of the first layer may be varied to reduce the impact of the solvent on the first drug. A finer spray and a larger distance, for example, may result in more evaporation of the solvent prior to contacting the first layer. In addition, the temperature of a spray nozzle or the ambient temperature may affect the amount of solvent that reaches the first layer, which higher temperatures tending to lead to greater evaporation of the solvent prior to reaching the first layer. The stability of the drugs at the elevated temperatures should be considered.

Any suitable spray system may be employed to spray the solution comprising the second drug and the solvent on the first layer on the device. The spray system may have any suitable nozzle. Preferably, the spray system is an ultrasonic spray system. For example, the spray system may comprise a Sono-Tek 8700-60 ultrasonic nozzle spray system or the like. Preferably, the spray system atomizes the solution.

The nozzle may be positioned any suitable distance from the surface of the device. For example, the nozzle may be positioned from about 1 cm to about 50 cm from the surface of the device, such as from about 5 cm to about 25 cm, or from about 7 cm to about 15 cm from the surface of the device.

The solution may be applied from the spray nozzle at any suitable flow rate. For example, the solution may be applied at a flow rate of about 0.01 microliters per second to about 100 microliters per second, such as from about 0.1 microliters per second to about 10 microliters per second, or from about 0.5 microliters per second to about 5 microliters per second.

The solution may be applied at any suitable temperature. Preferably the solution is applied at a temperature of from about 20° C. to about 25° C.

Employing the teachings presented herein, a device may be coated with a first crystalline drug and a second drug even if the first and second drugs have similar solubility characteristics. For example, the first and second drugs may be poorly water soluble (e.g., a solubility of less than 0.1 mg/ml in water, such as a solubility of less than 0.01 mg/ml in water, or less than 0.001 mg/ml in water, at room temperature). Despite paclitaxel and dexamethasone both being poorly water soluble, a solution comprising dexamethasone was able to be coated on a crystalline paclitaxel layer without altering the crystalline properties of the paclitaxel.

Referring now to FIG. 1, a sectional view of a medical device 400 is shown. The medical device 400 comprises a body 410 having exterior surface 404. A first layer 200 comprising a first drug, which may be crystalline, is disposed on the exterior surface 404 of the medical device 400. A second layer 500 comprising a second drug is disposed on the first layer 300. The body 410 may define an interior surface 102 defining an interior space 105. The device 400 may be or comprise, for example, an inflatable balloon or a stent.

Figure 2:
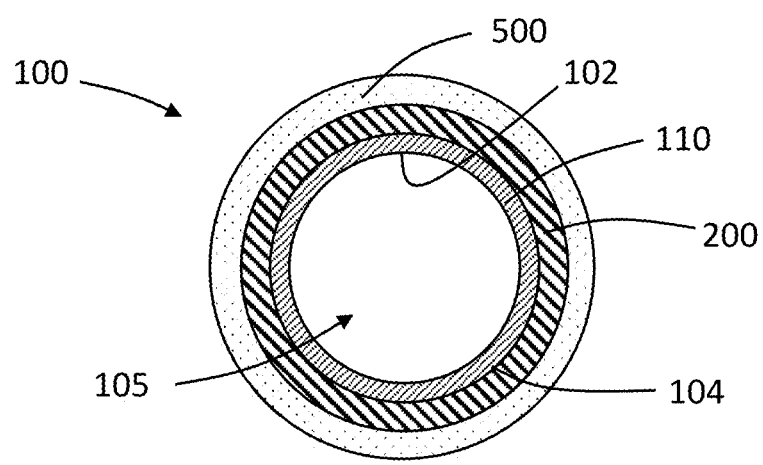
FIG. 2 is a schematic sectional view of an embodiment of an inflatable balloon having a coating comprising a nanoparticle or microparticle for releasing a therapeutic agent.

Referring now to FIG. 2, a sectional view of an inflated inflatable balloon 100 is shown. The inflatable balloon 100 comprises a body or wall 110 defining an interior surface 102 and an exterior surface 104, the interior surface 104 defining an interior space 105. A first layer 200 comprising a first drug, which may be crystalline, is disposed on the exterior surface 104 of the inflatable balloon 100. A second layer 500 comprising a second drug is disposed on the first layer 300.

EXAMPLES

In the following, non-limiting examples are presented illustrating proof of concept of various embodiments described herein. In some of the examples, a solution comprising dexamethasone "DEX") and a solvent are sprayed onto a surface on which crystalline paclitaxel ("PTX") is disposed, and the effect of the solvent on the crystalline form of PTX is determined. In some of the examples, the solution comprising dexamethasone also includes urea. In some examples, a solution comprising DEX and urea is sprayed on a first layer comprising crystalline sirolimus.

First Layer Comprising Crystalline PTX

It is noted that application of a single composition comprising a mixture of paclitaxel and dexamethasone did not result in crystalline paclitaxel on the surface. In contrast, spraying the dexamethasone, with or without urea, and solvent onto a surface of crystalline paclitaxel did not result in a single layer mixture of paclitaxel and dexamethasone, but rather resulted in two distinct and separate layers.

The first layer comprising crystalline paclitaxel also includes urea in some examples. A coating solution of paclitaxel (PTX) and urea is used. The coating solution contains a PTX-urea ratio for the drug coating solutions of 50:7 wt/wt. The PTX solvent-urea solvent ratio for the drug coating solutions is 90:10 v/v. The nominal drug dose density is 3.5 μg per mm².

A standard solution is prepared as follows:
PTX standard solution: 50 mg solubilized in 1 mL of THF
Urea standard solution: 1.25 g in 20 mL
PTX/urea standard solution: 90% PTX sol+10% Urea sol
DCB coating simulation: ≈60 microL of PTX/urea sol deposited on PA12 plate (area: 7.5 cm²—area comparable with 5.0×40 balloon; PTX content: ≈26 micrograms)

The paclitaxel-containing solution is uniformly deposited on a flat sample using a micropipette. The flat sample had an area of 7.5 cm². 2.6 mg of PTX is coated on the surface in a volume of 58.3 microliters.

FT-IR Spectroscopy Attenuated Total Reflectance (ATR) analysis of is performed to determine the crystal structure of the paclitaxel as follows:
Spectrophotometer: Thermo Scientific Nicolet iZ10
ATR accessory: Smart iTR (ZnSe)
Low wavenumber cutoff: 650 $cm^{-1}$
Depth of penetration: 2.03 micrometers at 1000 $cm^{-1}$
Refractive index: 2.4
Incident angle: 42°
Number of sample scans: 8
Number of background scans: 8
Solvents or solutions comprising dexamethasone (DEX) and a solvent are coated on the crystalline paclitaxel) using a Sono-Tek Ultrasonic Spray Nozzle System as follows:
Model: 8700-60
Max flow rate: 1,7 mL\s
Medial drop diameter: 31 μm Set-up:
Distance nozzle\sample: 10 cm
Stall point: 2,0 watts
Flow rate: 1 μL\s The solubility of DEX in various solvents is shown in Table 1 below.

TABLE 1

Solubility of DEX in various solvents

| Solvents | DEX solubility (mg\mL) |
| --- | --- |
| THF | 30 |
| Methanol | 15 |
| Acetone | 12 |
| Acetonitrile | 10 |
| Ethanol | 8 |

The effect on various solvents on the crystal structure of PTX/urea when coated on PTX/urea is shown in the Table 2 below.

TABLE 2

Effect of solvents (without DEX) on crystal structure of PTX/urea (Nylon12 plate area: 7.5 cm²)

| Solvents | Volume (μl) | Visual Inspection | FTIR-ATR |
| --- | --- | --- | --- |
| THF | 88 | Solubilization of coating components - doughy substance is obtained | Change in absorption bands |
| Methanol | 175 | Slightly wet | Unaffected |
| Acetone | 219 | Apparently unmodified | Unaffected |
| Acetonitrile | 263 | Apparently unmodified | Unaffected |
| Ethanol | 328 | Apparently unmodified | Unaffected |

The effect on various solutions comprising DEX and solvents on the crystal structure of PTX/urea when coated on PTX/urea is shown in Table 3 below.

TABLE 3

Effect of solvents (without DEX) on crystal structure of PTX/urea (Nylon12 plate area: 7.5 cm²)

| Solvents | Volume (μl) | FTIR-ATR (coating surface) | PTX morphology by FTIR-ATR evaluation |
| --- | --- | --- | --- |
| THF | 88 | DEX's absorption bands are evident | Changed |
| Methanol | 175 | DEX's absorption bands are evident | Unaffected |
| Acetone | 219 | DEX's absorption bands are evident | Unaffected |
| Acetonitrile | 263 | DEX's absorption bands are evident | Unaffected |
| Ethanol | 328 | DEX's absorption bands are evident | Unaffected |

While many of the solvents appear suitable, methanol and acetone show particular promise.

FTIR-ATR analysis of showing effects on PTX/urea and DEX is presented in the priority application (U.S. Provisional Application No. 62/772,997, filed on 29 Nov. 2018).

The following initial conclusions are drawn:
For each spectrum appear the main peaks of DEX.
No changes to the main PTX peaks.
Methanol is a good candidate because the DEX solubility is very high if comparted with other tested solvents.
Main advantages: minimization of the volume of the DEX solution to be sprayed and reduction of the time of the spraying process.

Further details regarding the methods, results and conclusions are presented in the priority application (U.S. Provisional Application No. 62/772,997, filed on 29 Nov. 2018).

Additional studies are performed to determine the effect of urea in the second layer comprising DEX. Solutions comprising DEX and urea are sprayed on nylon 12 balloons of NanoCross® Elite 6×80 balloons catheter (Medtronic, Inc.). A first layer comprising PTX and urea ("FreePac") are coated on the balloons per commercial coating recipes (e.g., Medtronic, Inc.'s IN.PACT™ Admiral™ drug-coated balloon). The balloons are tracked through a simulated use model with a sheath inserted, the balloon is tracked through the sheath and when it is beyond the sheath it is tracked into a beaker and then deployed (inflated). The average amount of drug lost during tracking, the average amount of drug released in the beaker, and the average amount of drug remaining on the balloon is determined after two tracking and deployment runs.

The effect of urea in the second layer comprising DEX is determined by comparing drug release in the presence and absence of urea in the second layer. The first layer comprising PTX is applied as described above. The second layer comprising DEX or DEX and urea are generally applied as described above. The following solutions comprising DEX or DEX and urea were applied to the first layer comprising crystalline PTX:

DEX in methanol
DEX/urea (1:1, w/w) in methanol
DEX/urea (1:1, w/w) in ethanol/water (99:1)

One percent water was used with ethanol to provide better solubility for urea.

Table 4 below provides information regarding the solutions prepared for spraying the second layer on the device.

TABLE 4

Solutions of DEX or DEX/urea (Nylon12 plate area: 7.5 cm$^2$)

| Solvents | Urea (mg) | DEX (mg) | Volume (µl) |
|---|---|---|---|
| Methanol | 0 | 2.6 | 175 |
| Methanol | 2.6 | 2.6 | 175 |
| Ethanol/water (99:1) | 2.6 | 2.6 | 328 |

The balloons were coated with about 4 to 6 mg PTX and about 4 to 6 mg DEX, with an average of about 5 mg of each of PTX and DEX.

Table 5 below provides results of tracking and deployment experiments.

| Test Article | PTX released in beaker | PTX remaining on balloon | PTX lost during tracking | DEX released in beaker | DEX remaining on balloon | DEX lost during tracking |
|---|---|---|---|---|---|---|
| DEX Methanol | 4.3% | 51.7% | 44% | 1.2% | 21% | 77.8% |
| DEX/urea Methanol | 9.5% | 34% | 56.5% | 1.4% | 9.5% | 89.1% |
| DEX/urea ETOH/water | 9.9% | 26% | 64.1% | 2.0% | 10.5% | 87.5% |

As indicated in Table 5, the presence of urea in the second (DEX) layer improved release of the PTX in the first layer as well as DEX in the second layer, which did result in additional drug loss during tracking. Increased release is believed to result in increased drug transfer to a vessel when applied in vivo.

Figure 3:
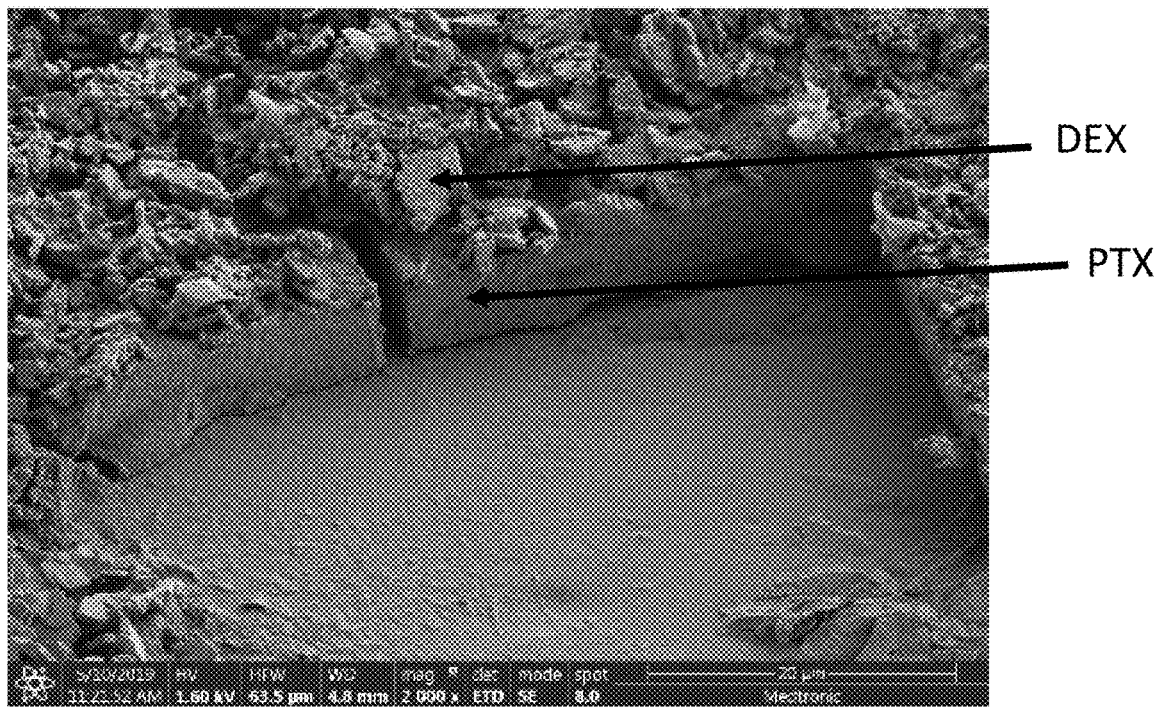
FIGS. 3 and 4 are scanning electron micrographic images of a device coated with a first layer comprising crystalline paclitaxel (PTX) and a second layer comprising dexamethasone (DEX) and urea at 2000× magnification (FIG. 3) and 10,000× magnification (FIG. 4).
Figure 4:
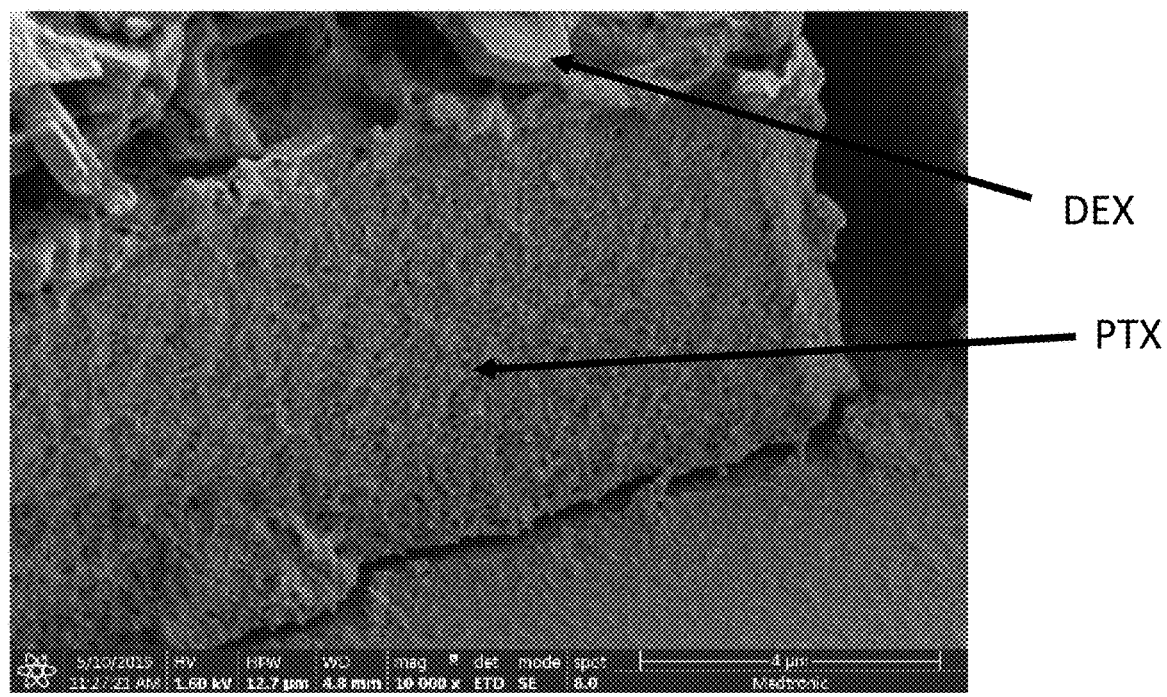

FIGS. 3-4 show scanning electron micrographic images of a device coated with a first layer comprising crystalline paclitaxel (PTX) and a second layer comprising dexamethasone (DEX) and urea at 2000× magnification (FIG. 3) and 10,000× magnification (FIG. 4). The DEX/urea was sprayed on the crystalline PTX layer using the DEX/urea in ethanol/water (99:1) solvent. Two distinct layers are shown, and the PTX maintains its crystalline form.

First Layer Comprising Sirolimus

Additional studies are performed to determine the effect of coating a second layer comprising DEX and urea onto a first layer comprising crystalline sirolimus.

A sirolimus/urea (1,000:1, w/w) in ethyl acetate/heptane (5:3, v/v) coating is applied to catheter balloons. Briefly, sirolimus is dissolved in ethyl acetate (about 110 mg/ml) under stirring and heptane is slowly added under stirring until an ethyl acetate/heptane ratio of 5:3 v/v is obtained. A volume of urea dissolved in methanol (about 100 mg/ml) to achieve a sirolimus/urea ratio of 1000:1 (w/w) is added to result in a coating solution. 158 µl of coating solution is sprayed onto a nylon 12 balloon if a NanoCross® Elite 6×80 drug-coated balloon catheter, the balloon having a surface area of 16.6 cm$^2$ to achieve a sirolimus density of about of 7 µg/mm$^2$. The solvent is dried leaving a coating comprising a mixture of amorphous and crystalline sirolimus, with about 15% being crystalline (data not shown).

DEX and urea (1:1, w/w) are dissolved in ethanol/water (99:1, v/v) at about 15 mg/ml each. 363 µl (about 5.8 mg of each of DEX and urea) is sprayed onto the previously coated sirolimus layer to achieve a DEX density of about 3.5 µg/mm$^2$. The DEX/urea spray coating process adversely impacts the morphology of the sirolimus coating. That is, minimal crystalline sirolimus remains (data not shown). The DEX is crystalline (date not shown).

As indicated in the disclosure above, modification of the solvent used to dissolve the DEX or the process conditions may result in better retention of crystalline sirolimus in the underlying coating. For example, a finer spray or spraying of the DEX coating from a further distance may aid in maintaining crystallinity of sirolimus; increasing the temperature of the spray at the nozzle may aid in maintaining crystallinity of the sirolimus; use of a more volatile solvent for the DEX may aid in maintaining crystallinity of sirolimus; use of a solvent that is better for DEX than for sirolimus may aid in maintaining crystallinity of sirolimus; etc. In addition or alternatively, the DEX may be dissolved in the solvent that was used to apply the sirolimus layer may be beneficial in maintaining crystallinity of sirolimus, because if the sirolimus is dissolved in the solvent it may recrystallize when the solvent evaporates.

While the process of coating the DEX/urea on the sirolimus adversely affects the morphology (less crystalline sirolimus), the coating appears to improve flaking and cracking (minimal cracking and flaking), surface roughness (smooth), and porosity (no pores) relative to the sirolimus coating alone (deep cracking and substantial flaking, rougher surface, and small pores) upon visual inspection of scanning electron microscope images (data not shown). Such results may result in improved drug release.

The coated balloons were inflated against tissue in an ex-vivo model. Briefly, the model included a bovine carotid artery mounted in a simulated flow loop comprising appropriately sized tubing. The system was maintained at 37° C. A standard hemostasis valve and 8 Fr introducer sheath are used to introduce the coated balloon into the tubing, the balloon is tracked through the sheath and tubing into the bovine carotid artery, and the balloon is deployed (inflated to approximately 1.1 B.A.R. and held for 60 s) against the bovine carotid artery tissue. The tissue and balloon are removed for analysis. The amount of drug (sirolimus and DEX) lost during tracking, retained on the balloon, and transferred to the bovine carotid artery tissue are determined. Briefly, the amount of drug was measured by using HPLC of extracted solutions from testing specimens, such as utilizing a solvent to solubilize and remove all remaining drug from the balloon for analysis.

About 1.7 percent of the sirolimus is transferred to the tissue (tissue concentration average of about 25.9 μg sirolimus/g of tissue, n=5), about 81.8% was lost during tracking, and about 16.5% remained on the balloon. About 15.1 percent of the DEX is transferred to the tissue (tissue concentration average of about 22.6 μg DEX/g of tissue, n=5), about 46.9% was lost during tracking, and about 38.0% remained on the balloon.

In vivo studies are also performed. Briefly, in a porcine model, carotid access was achieved with a 8 Fr introducer sheath and devices were inserted and tracked to the target vessels (internal and external femoral arteries) where they were deployed (inflated) to a target BAR of 1.3 and held inflated for 3 minutes prior to being deflated and removed from the animal. After 1 day, the median sirolimus concentration in the tissue is about 0.62 μg/g, and after 28 days the median concentration is about 0.07 μg/g (n=18). After 1 day, the median DEX concentration in the tissue is about 0.000525 μg/g, and after 28 days the median concentration is about 0.0005 μg/g (n=18). DEX was detectable in four of six vessels after 1 day and in two of six vessels at day 28.

SUMMARY OF SOME ILLUSTRATIVE EMBODIMENTS

Below, there is provided a non-exhaustive numbered list of non-limiting examples. Any one of the features of these examples may be combined with any other feature of another example, specific embodiment, or aspect of the invention described herein.

1: A method for coating a medical device comprising a first layer comprising a first drug, wherein the first layer is free from polymers and the first drug is an antiproliferative agent, the method comprising:
　applying a solution comprising a second drug and a solvent to form a second layer on the first layer of the medical device, wherein the second drug is an anti-inflammatory agent and the second layer is free from polymers.
2: The method of example 1, wherein the first drug in the first layer is in crystalline form and wherein the solution comprising the second drug is applied to the first layer of the medical device such that the first drug maintains its crystalline form.
3: The method of example 1 or 2, wherein the first drug is a taxol or limus-derivative.
4: The method of example 1 or 2, wherein the first drug is rapamycin, taxol, paclitaxel, doxetaxel, sirolimus, rapamycin, everolimus, or zotarolimus.
5: The method of example 1 or 2, wherein the first drug is paclitaxel.
6: The method of example 5, wherein the solvent comprises one or more of tetrahydrofuran, methanol, acetonitrile, dimethyl sulfoxide, dioxane, ethanol, and water.
7: The method of example 6, wherein the solvent comprises less than 15% water by volume.
8: The method of example 5 or 6, wherein the solvent comprises methanol or acetone.
9: The method of any one of the preceding examples, wherein the second drug is a glucocorticoid.
10: The method of any one of the preceding examples, wherein the second drug is dexamethasone.
11: The method of any one of any one of the preceding examples, wherein applying the solution comprises spraying the solution.
12: The method of example 11, wherein spraying the solution comprises ultrasonically spraying the solution.
13: The method of any one of the preceding examples, wherein the medical device comprises a balloon or a stent.
14: The method of example 13, wherein the medical device comprises a balloon.
15: A medical device comprising
　a body,
　a first layer on the body, wherein the first layer comprises a first drug, wherein the first layer is free from polymers and the first drug is an antiproliferative agent; and
　a second layer on the first layer, wherein the second layer comprises a second drug, wherein the second drug is an anti-inflammatory agent and the second layer is free from polymers.
16: The medical device of example 15, wherein the first drug in the first layer is in crystalline form.
17: The medical device of example 15 or 16, wherein the first drug is paclitaxel and the second drug is dexamethasone.
18: The medical device of any one of examples 15 to 17, wherein the medical device comprises a balloon or a stent.
19: The medical device of any one of examples 15 to 17, wherein the medical device comprises a balloon.

Thus, embodiments of DRUG COATED MEDICAL DEVICES are disclosed. One skilled in the art will appreciate that the nanoparticles or microparticles and methods described herein can be practiced with embodiments other than those disclosed. The disclosed embodiments are presented for purposes of illustration and not limitation.

What is claimed is:
1. A method for coating a medical device comprising a first layer comprising a first drug, wherein the first layer is free from polymers and the first drug is an antiproliferative agent, the method comprising:
　applying a solution comprising a second drug and a solvent to form a second layer on the first layer of the medical device, wherein the second drug is an anti-inflammatory agent and the second layer is free from polymers, wherein the first drug in the first layer is in crystalline form and wherein the solution comprising the second drug is applied to the first layer of the medical device such that the first drug maintains its crystalline form.

2. The method of claim 1, wherein the first drug is a taxol or limus-derivative.

3. The method of claim 1, wherein the first drug is rapamycin, taxol, paclitaxel, doxetaxel, sirolimus, rapamycin, everolimus, or zotarolimus.

4. The method of claim 1, wherein the first drug is paclitaxel.

5. The method of claim 4, wherein the solvent comprises one or more of tetrahydrofuran, methanol, acetonitrile, dimethyl sulfoxide, dioxane, ethanol, and water.

6. The method of claim 5, wherein the solvent comprises less than 15% water by volume.

7. The method of claim 5, wherein the solvent comprises methanol or acetone.

8. The method of claim 1, wherein the second drug is a glucocorticoid.

9. The method of claim 1, wherein the second drug is dexamethasone.

10. The method of claim 1, wherein applying the solution comprises spraying the solution.

11. The method of claim 10, wherein spraying the solution comprises ultrasonically spraying the solution.

12. The method of claim 1, wherein the medical device comprises a balloon or a stent.

13. The method of claim 12, wherein the medical device comprises a balloon.

14. A medical device comprising
a body,
a first layer on the body, wherein the first layer comprises a first drug, wherein the first layer is free from polymers and the first drug is an antiproliferative agent; and
a second layer on the first layer, wherein the second layer comprises a second drug, wherein the second drug is an anti-inflammatory agent and the second layer is free from polymers,
wherein the first drug in the first layer is in crystalline form.

15. The medical device of claim 14, wherein the first drug is paclitaxel and the second drug is dexamethasone.

16. The medical device of claim 14, wherein the medical device comprises a balloon or a stent.

17. The medical device of claim 14 wherein the medical device comprises a balloon.

* * * * *